United States Patent
Lavedan et al.

(10) Patent No.: US 8,652,776 B2
(45) Date of Patent: Feb. 18, 2014

(54) PREDICTION OF QT PROLONGATION BASED ON SNP GENOTYPE

(75) Inventors: Christian Lavedan, Potomac, MD (US); Simona Volpi, Derwood, MD (US); Louis Licamele, Gaithersburg, MD (US); Kendra Tomino Mack, Westminster, MD (US); Callie Michelle Heaton, Washington, DC (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 720 days.

(21) Appl. No.: 12/675,607

(22) PCT Filed: Sep. 10, 2008

(86) PCT No.: PCT/US2008/075905
§ 371 (c)(1), (2), (4) Date: Feb. 26, 2010

(87) PCT Pub. No.: WO2009/036100
PCT Pub. Date: Mar. 19, 2009

(65) Prior Publication Data
US 2010/0249188 A1    Sep. 30, 2010

Related U.S. Application Data

(60) Provisional application No. 60/971,232, filed on Sep. 10, 2007.

(51) Int. Cl.
*C12Q 1/68* (2006.01)
*C07H 21/02* (2006.01)
*C07H 21/04* (2006.01)

(52) U.S. Cl.
USPC .......... 435/6.1; 435/6.11; 536/23.1; 536/24.3

(58) Field of Classification Search
None
See application file for complete search history.

(56) References Cited

U.S. PATENT DOCUMENTS

| | | | |
|---|---|---|---|
| 5,364,866 A | 11/1994 | Strupczewski et al. | |
| 2003/0091645 A1 | 5/2003 | Ahlheim et al. | |
| 2006/0073506 A1* | 4/2006 | Christians et al. | 435/6 |
| 2006/0204486 A1 | 9/2006 | Pyke et al. | |

FOREIGN PATENT DOCUMENTS

| | | |
|---|---|---|
| WO | 9309276 A1 | 5/1993 |
| WO | 9511680 A1 | 5/1995 |
| WO | 0222875 A2 | 3/2002 |
| WO | 0222875 A3 | 3/2002 |
| WO | 03020707 A1 | 3/2003 |
| WO | 2004006886 A2 | 1/2004 |
| WO | 2008012199 A2 | 1/2008 |
| WO | 2008121899 A2 | 10/2008 |
| WO | 2008121899 A3 | 10/2008 |

OTHER PUBLICATIONS

GenBank dbSNP information for rs993648 added with build 86 on Oct. 16, 2000. http://www.ncbi.nlm.nih.gov/projects/SNP/snp_ref.cgi?rs=993648.*
Syvanven, Ann-Christine. Nature Reviews Genetics Dec. 2001 vol. 2 pp. 930-942.*
Ss23738281 (dbSNP, rs3924426; 2004).*
Hegele (Arterioscler. Thromb. Vasc. Biol.; 2002, vol. 22, pp. 1058-1061).*
Lucentini (The Scientist; 2004, vol. 24, p. 20).*
Juppner (Juppner; Bone, vol. 17; 1995, pp. 39S-40S).*
Patent Cooperation Treaty, PCT Notification of Transmittal of The International Search Report and The Written Opinion of the International Searching Authority, or the Declaration, dated Jul. 3, 2009 for Application No. PCT/US2008/075905, filed Sep. 10, 2008, 19 pages.
Sesti, et al., "A Common Polymorphism Associated With Antibiotic-Induced Cardiac Arrhythmia", Sep. 2000, pp. 10613-10618, XP002233721, PNAS, vol. 97, No. 19 (www.pnas.org).
NCBI, Single Nucleotide Polymorphism, pp. 1-4, Nov. 30, 2009, XP-002518809, submitted SNP(ss) Details: ss1451062.
European Patent Office, Office Action for Application Serial No. 08830208.8 dated Aug. 17, 2010, 7 pages.
European Patent Office, Office Action for Application Serial No. 08830208.8 dated Apr. 14, 2011, 3 pages.
Patent Cooperation Treaty, International Preliminary Report on Patentability and Written Opinion of the International Searching Authority for PCT/US2008/075905 dated Mar. 25, 2010, 10 pages.

* cited by examiner

*Primary Examiner* — Jehanne Sitton
(74) *Attorney, Agent, or Firm* — Hoffman Warnick LLC (57) ABSTRACT

The present invention relates to the prediction of QT prolongation following administration of a compound capable of increasing an individual's QT interval based on the individual's genotype at one or more single nucleotide polymorphism (SNP) loci and to the treatment of a patient based on such prediction.

8 Claims, 3 Drawing Sheets

PREDICTION OF QT PROLONGATION BASED ON SNP GENOTYPE

CROSS-REFERENCE TO RELATED APPLICATIONS

This application claims the benefit of U.S. Provisional Patent Application No. 60/971,232, filed 10 Sep. 2007, which is hereby incorporated herein.

SEQUENCE LISTING

The sequence listing contained in the electronic file titled "VAND-0057-PCT_Seq_Ms.txt," created 10 Sep. 2008, comprising 4 KB, is hereby incorporated herein.

BACKGROUND OF THE INVENTION

QT prolongation is an electrographic repolarization abnormality of the cardiac muscle that can cause syncope, distinctive ventricular tachycardia (e.g., torsades de pointes), and, in rare cases, sudden cardiac death. Many drugs, including antipsychotics, have the potential to prolong the QT interval by blocking the rapidly activating delayed rectifier current ($I_{kr}$). Recent evidence suggests that only 5% to 15% of persons who experience drug-induced torsades de pointes carry a mutation in one of the ion channel genes associated with hereditary long QT syndrome (LQTS). It is likely that other genes and environmental factors contribute to drug-induced LQTS. Although there is a poor correlation between the extent of QT prolongation and the occurrence of torsades de pointes, identifying new genetic factors that predispose patients to drug-induced QT prolongation may help in understanding and preventing this type of ventricular tachycardia.

SUMMARY OF THE INVENTION

The present invention relates to the prediction of QT prolongation following administration of a compound capable of increasing an individual's QT interval based on the individual's genotype at one or more single nucleotide polymorphism (SNP) loci and to the treatment of a patient based on such prediction.

One aspect of the invention provides a method of predicting an individual's QT prolongation following administration of a compound capable of prolonging the individual's QT interval, the method comprising: determining the individual's genotype at least one single nucleotide polymorphism (SNP) locus selected from a group consisting of: rs993648, rs3924426, rs4799915, rs4933824, rs714881, and rs17054392; and in the case that the individual's genotype at the at least one SNP locus is associated with increased QT prolongation, predicting that the individual will experience above-average QT prolongation. Such compounds include, atypical antipsychotics, such as, for example, iloperidone, clozapine, risperidone, olanzapine, quetiapine, siprasidone, aripiprazole, paliperidone, asenapine, sertindole, zotepine, amisulpride, bifeprunox, melperone, pharmaceutically-acceptable salts thereof, metabolites thereof, and pharmaceutically-acceptable salts of metabolites thereof.

Another aspect of the invention provides a method of predicting an individual's QT prolongation following administration of a compound capable of prolonging the individual's QT interval, the method comprising: determining the individual's genotype at least one single nucleotide polymorphism (SNP) locus selected from a group consisting of: rs993648, rs3924426, rs4799915, rs4933824, rs714881, and rs17054392; and in the case that the individual's genotype at the at least one SNP locus is associated with decreased QT prolongation, predicting that the individual will experience below-average QT prolongation.

Yet another aspect of the invention provides a method of treating a patient for one or more symptoms of a psychotic disorder, the method comprising: determining the patient's genotype in both copies of at least one single nucleotide polymorphism (SNP) locus selected from a group consisting of: rs993648, rs3924426, rs4799915, rs4933824, rs714881, and rs17054392; and treating the patient based upon whether the patient's genotype at the at least one SNP locus is associated with increased QT prolongation.

Still another aspect of the invention provides a method of administering to an individual a compound capable of prolonging the individual's QT interval, the method comprising: determining at least a portion of an individual's ceramide kinase-like (CERKL) gene sequence; and in the case that a portion of the individual's CERKL gene sequence is associated with an increased risk of QT prolongation, performing at least one of the following: administering to the individual a quantity of the compound less than would be administered to an individual having a CERKL gene sequence not associated with an increased risk of QT prolongation, administering to the individual a quantity of the compound equal to that which would be administered to an individual having a CERKL gene sequence not associated with an increased risk of QT prolongation; or monitoring the patient for QT prolongation; or electing instead to treat the individual with a different compound not known to be associated with QT prolongation.

Another aspect of the invention provides a kit for use in determining treatment strategy for a patient with a psychotic disorder, schizophrenia, or bipolar disorder comprising: at least one polynucleotide able to recognize and bind to a portion of DNA containing a single nucleotide polymorphism (SNP) selected from a group consisting of: rs993648, rs3924426, rs4799915, rs4933824, rs714881, and rs17054392; a container suitable for containing the at least one polynucleotide and a sample of chromosomal DNA from the said individual wherein the at least one polynucleotide can contact the chromosomal DNA; and means to detect the combination of the at least one polynucleotide with the chromosomal DNA and thereby to ascertain what the genotype of the individual is at the SNP.

Yet another aspect of the invention provides iloperidone, an active metabolite of iloperidone, or a salt of iloperidone or of an active metabolite of iloperidone for use in the treatment of patients suffering from one or more symptoms of a psychotic disorder, schizophrenia, or bipolar disorder in a patient that has a genotype that is associated with increased QT prolongation at least one of the SNP locus selected from a group consisting of: rs993648, rs3924426, rs4799915, rs4933824, rs714881, and rs17054392 SNPs.

DETAILED DESCRIPTION OF THE INVENTION

Iloperidone (1-[4-[3-[4-(6-fluoro-1,2-benzisoxazol-3-yl)-1-piperidinyl]propoxy]-3-methoxyphenyl]ethanone) is disclosed in U.S. Pat. No. 5,364,866, which is incorporated herein by reference. Active metabolites of iloperidone are useful in the present invention. See, e.g., WO03020707, which is incorporated herein by reference. Iloperidone metabolites include: 4-[3-[4-(6-Fluoro-1,2-benzisoxazol-3-yl)-1-piperidinyl]propoxy]-3-methoxy-α-methylbenzene methanol, 1-[4-[3-[4-(6-Fluoro-1,2-benzisoxazol-3-yl)-1-piperidinyl]propoxy]-3-hydroxyphenyl]ethanone, 1-[4-[3-[4-(6-Fluoro-1,2-benzisoxazol-3-yl)-1-piperidinyl]propoxy]-3-methoxyphenyl]-2-hydroxyethanone, 4-[3-[4-(6-Fluoro-1,2-benzisoxazol-3-yl)-1-piperidinyl]propoxy]-3-hydroxy-α-methylbenzene methanol, 4-[3-[4-(6-Fluoro-1,2-benzisoxazol-3-yl)-1-piperidinyl]propoxyl-2-hydroxy-5-methoxy-α-methylbenzene methanol, 1-[4-[3-[4-(6-Fluoro-1,2-benzisoxazol-3-yl)-1-piperidinyl]propoxy]-2-hydroxy-5-methoxyphenyl]ethanone, and 1-[4-[3-[4-(6-Fluoro-1,2-benzisoxazol-3-yl)-1-piperidinyl]propoxy]-2,5-dihydroxyphenyl]ethanone. See, U.S. Pat. No. 5,364,866, WO93/09276 and WO95/11680, which are incorporated herein by reference.

An effective amount of iloperidone or an active metabolite thereof may be administered to a subject animal (typically a human but other animals, e.g., farm animals, pets and racing animals, can also be treated) by a number of routes. An effective amount is an amount that during the course of therapy will have a preventive or ameliorative effect on a psychotic disorder, such as schizophrenia, or a symptom thereof. An effective amount, quantitatively, may vary, depending upon, for example, the patient, the severity of the disorder or symptom being treated, and the route of administration.

It will be understood that the dosing protocol including the amount of iloperidone or an active metabolite thereof actually administered will be determined by a physician in the light of the relevant circumstances including, for example, the condition to be treated, the chosen route of administration, the age, weight, and response of the individual patient, and the severity of the patient's symptoms. Patients should of course be monitored for possible adverse events.

For therapeutic or prophylactic use, iloperidone or an active metabolite thereof will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions may be prepared by conventional techniques appropriate to the desired preparation containing appropriate amounts of iloperidone or an active metabolite thereof. See, for example, Remington's Pharmaceutical Sciences, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form. The term "unit dosage form" refers to physically discrete units suitable as unitary dosages for human subjects and other mammals, each unit containing a predetermined quantity of active material calculated to produce the desired prophylactic or therapeutic effect over the course of a treatment period, in association with the required pharmaceutical carrier.

Iloperidone and its active metabolites can also be formulated in a controlled release form, e.g., delayed, sustained, or pulsatile release.

Various formulations and methods of administering iloperidone and/or its derivatives have been described. For example, PCT Publication No. WO 2004/006886 A2 describes an injectable depot formulation comprising iloperidone crystals, microencapsulated depot formulations of iloperidone and a polyglycolide polylactide glucose star polymer are described in U.S. 20030091645 each of which is incorporated herein by reference.

Iloperidone, like other typical and atypical antipsychotics, has been observed to have some effects on QT interval duration Importantly, no evidence to date indicates that any patient treated with iloperidone has experienced torsades de pointes. To identify new genetic markers of drug-induced QT prolongation, a whole genome association study (WGAS) was conducted as part of a phase 3 clinical trial of iloperidone. The clinical trial was a randomized, double-blind, placebo-, and ziprasidone-controlled multicenter study evaluating the efficacy, safety, and tolerability of a 24 mg/day dose of iloperidone administered twice a day (bid) for 28 days to patients with schizophrenia in acute exacerbation.

The effect of iloperidone on the QT interval was shown to be greatest by Day 14, when iloperidone achieves steady state concentrations. Therefore, the change in QT interval was calculated between baseline and Day 14. The Fridericia correction (QTcF) was applied, and a generalized linear model (GLM) statistical analysis using baseline as a covariate was performed. Of the 334,563 single nucleotide polymorphisms (SNPs) analyzed, 23 SNPs from 18 distinct chromosome regions had a BH-adjusted P<0.2 after false discovery rate (FDR) correction, all with raw P<0.000005. Analysis was focused on those SNPs located within or close to genes (<10 kb away) in which the minor genotype group included at least 10% of the patients. Six SNPs of interest were identified in the CERKL, SLCO3A1, BRUNOL4, NRG3, NUBPL, and PALLD genes (Table 1). The possibility that changes in the QT interval reflect drug concentration differences could not be excluded because drug exposure at the time of electrocardiography (ECG) was not known. However, the six SNPs identified here are within genes not expected to play roles in drug absorption, metabolism, or excretion. For these SNPs, genotype calls generated by the microarray set were confirmed by sequencing on a random subset of DNA samples of iloperidone-treated patients. The association of a particular genotype class with lower or higher increased QT was consistent between men and women and across races. Additional SNPs with statistical association at P<0.001 were observed within or near the CERKL, SLCO3A1, NRG3, NUBPL, and PALLD genes (FIGS. 1a-f).

SNP rs993648 is located within intron 2 of the CERKL gene (FIG. 1a), which codes for a ceramide kinase-like protein. Patients treated with iloperidone who were heterozygous for rs993648 had a mean QTcF change of 4.5 msec compared with 17.8 msec for homozygous patients ($P=2.83\times10^{-6}$) (Table 1). The CERKL protein has sequence similarity with a ceramide kinase coded by another gene, CERK, and with sphingosine kinases 1 and 2. Ceramide kinases convert the sphingolipid ceramide to ceramide-1-phosphate. Several studies have demonstrated that ceramide regulates transmembrane currents conducted by various potassium channels, including hERG. The hERG channel underlies the rapid component of the delayed rectifier current ($I_{Kr}$), which contributes to the repolarization of the cardiac action potential. It has been shown that ceramide down-regulates surface expression of the hERG protein and evokes a decrease in the hERG current. The action of ceramide on ion channels is thought to be mediated mainly by kinase activity. Little is known about the function of the CERKL protein, and in vitro experiments have failed to demonstrate that CERKL can actually phosphorylate ceramides. The binding affinity of the CERKL protein for ceramide and ceramide derivatives and the identity of cofactors that may play a role in its in vivo activities remain to be explored. It is unclear at this time, why the heterozygous would confer a different phenotype than either heterozygous genotype. Several CERKL isoforms have been described, but it is unknown whether they are associated with specific allelic variants and whether they interact as heterodimers. Our results suggest that studying the involvement of CERKL and, more broadly, the ceramide pathway may lead to better understanding of the mechanism of QT prolongation induced by antipsychotic medications or other drugs known to affect the QT interval.

Figure 1A:
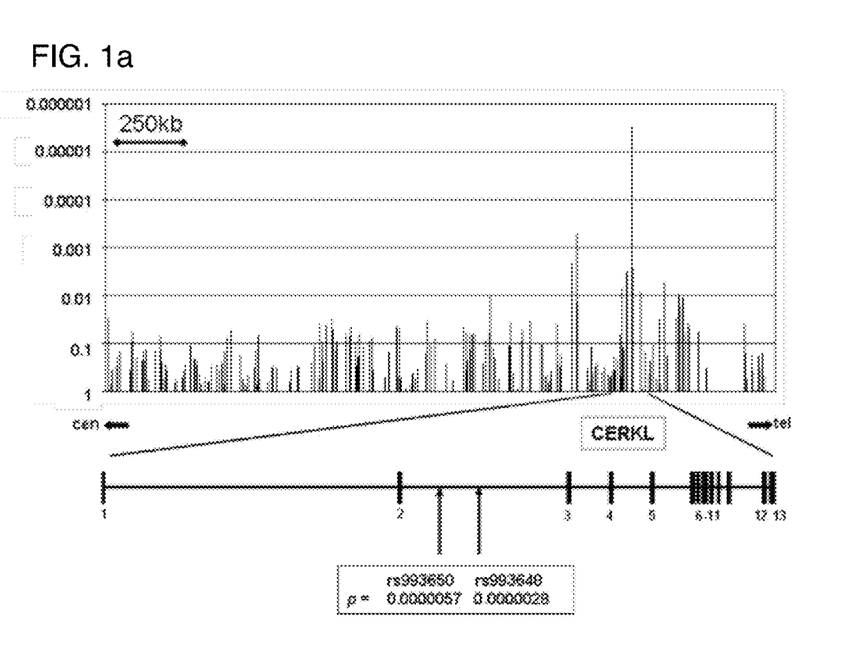
FIGS. 1a-f show genetic associations between change in QTcF and SNPs in the CERKL, SLCO3A1, BRUNOL4, NRG3, NUBPL, and PALLD gene regions. P values (vertical axis) from the GLM analysis are shown for the genomic regions containing CERKL (1a), SLCO3A1 (1b), BRUNOL4 (1c), NRG3 (1d), NUBPL (1e), and PALLD (1f) in order of the physical location of the SNP (horizontal axis). The direction of the maps relative to the centromere (cen) and the telomere (tel) is indicated by horizontal arrows. SNPs with P≤0.001 are boxed. The approximate location of exons is shown by vertical bars, with corresponding numbers below.
Figure 1B:
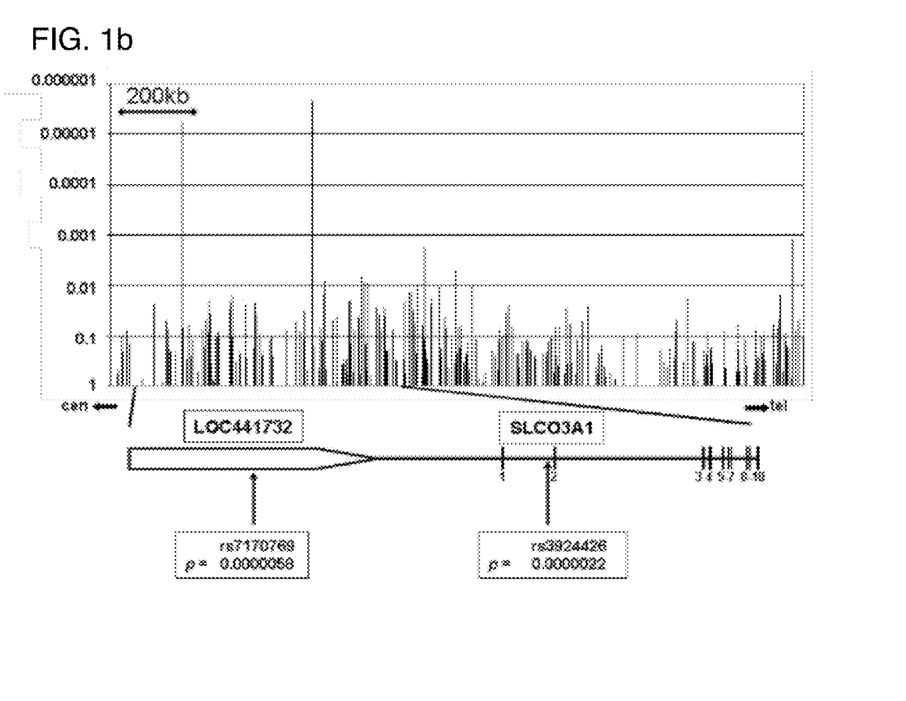
Figure 1C:
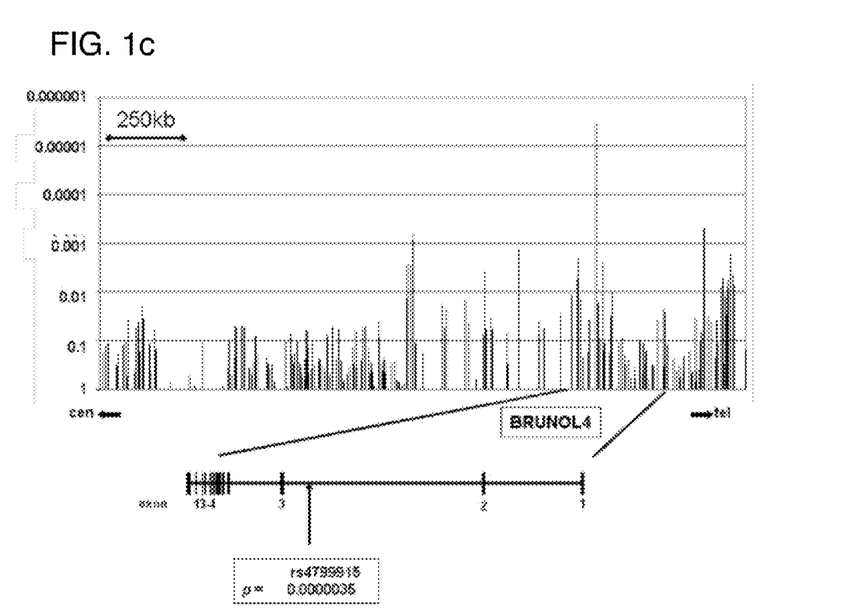

SNP rs3924426 is located within intron 1 of the SLCO3A1 gene (FIG. 1b). SLCO3A1 encodes the solute carrier organic anion transporter family, member 3A1, known as organic anion transporting polypeptide, subtype D (OATP-D). Patients who carried the rs3924426 non-TT genotype had a mean QTcF change of 2.5 msec compared with 15.0 msec for the homozygous TT patients. OATP-D is predominantly expressed in the brain, testis, and heart, particularly in the myocardium, vascular endothelium, and coronary artery. In addition, OATP-D plays an important role in translocating prostaglandins E1, E2, and F2α in specialized cells and tissues. It has been shown that prostaglandins have cardioprotective effects and that, in particular, prostaglandin E2 can prevent torsades de pointes in rabbits treated with the antiarrhythmic drug clofilium. The results described here provide the first evidence of a possible direct link between SLCO3A1 and myocardial repolarization.

SNP rs4799915 is located within intron 2 of the BRUNOL4 gene (FIG. 1c), which codes for the RNA binding protein bruno-like 4. Patients who carried the rs4799915 CC genotype had a mean QTcF change of 2.9 msec compared with 14.5 msec for patients with a different genotype (Table 1). The BRUNOL4 gene product, CELF4, belongs to a family of RNA-binding proteins (BRUNOL or CELF proteins) that regulate pre-mRNA alternative splicing and that may be involved in mRNA editing and translation. The BRUNOL2 and BRUNOL3 proteins are known as CUGBP1 and CUGBP2 because of their ability to bind the trinucleotide CUG repeat. These proteins are highly expressed in the heart, and it has been suggested that they play a role in the pathogenesis of various skeletal muscle and heart diseases. Transgenic mice with a nuclear dominant-negative CELF4 protein, which was expressed specifically in the heart, exhibited defects in the alternative splicing of pre-mRNA and developed cardiac hypertrophy, dilated cardiomyopathy, severe cardiac dysfunction, and premature death. This phenotype was rescued by increased cardiac expression of a wild-type CELF protein. CELF proteins may play a key role in the regulation of alternative splicing crucial in the maintenance of normal cardiac structure and function. It would be of interest to further investigate how this protein family may be involved in myocardial repolarization, particularly CELF4, which was associated in our study with drug-induced QT prolongation.

Figure 1D:
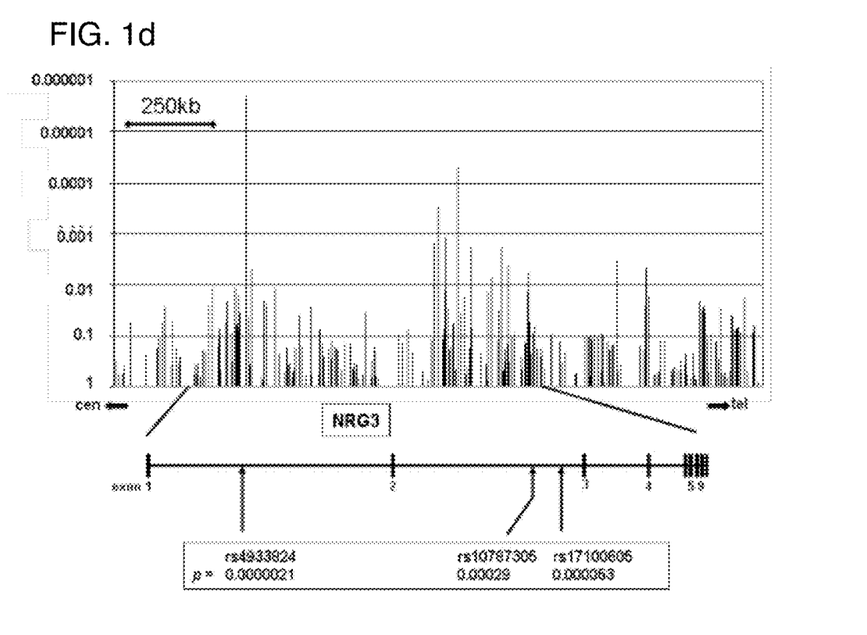

SNP rs4933824 is located within intron 1 of the neuregulin 3 (NRG3) gene (FIG. 1d). Patients who carried the rs4933824 non-GG genotype had a mean QTcF change of 4.4 msec compared with 15.3 msec for patients with a different genotype (Table 1). Neuregulins are growth and differentiation factors related to epidermal growth factor, and they are ligands for receptor tyrosine kinases of the ErbB family. Expression of NRG1 has been observed in primary cultures of coronary microvascular endothelial cells. It has been shown that a recombinant form of NRG1 promotes the proliferation of embryonic cardiac myocytes and the growth and survival of ventricular myocytes in vitro. These observations led to the suggestion that the neuregulin-ErbB signaling system plays an important role in the onset of myocardial trabeculation and cardiac morphogenesis. What role neuregulin 3 plays in myocardial repolarization remains to be explored.

Figure 1E:
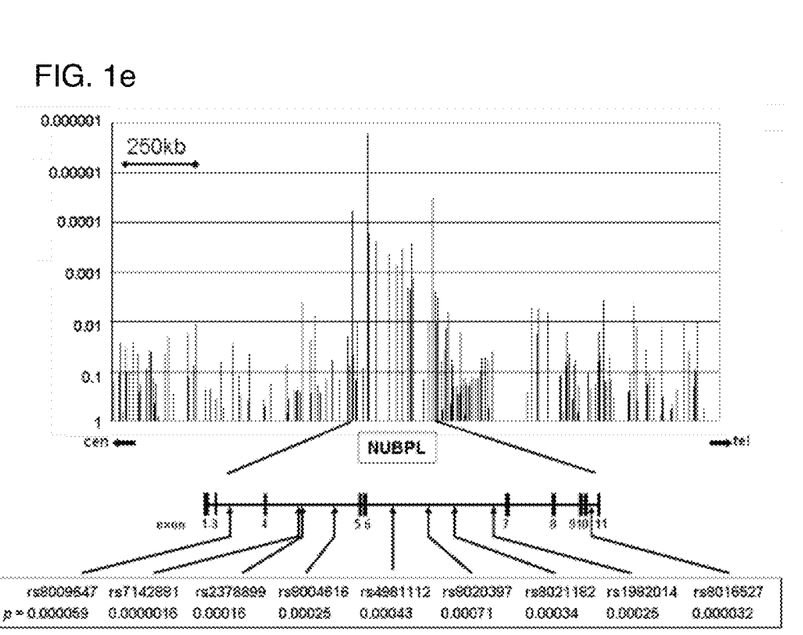

SNP rs7142881 is located within intron 4 of the nucleotide binding protein-like (NUBPL) gene (FIG. 1e). Patients who carried the rs7142881 GG genotype had a mean QTcF change of 5.7 msec compared with 16.7 msec for patients with a different genotype (Table 1). At this time, the site(s) of expression of the NUBPL gene and the function of the encoded protein are unknown.

Figure 1F:
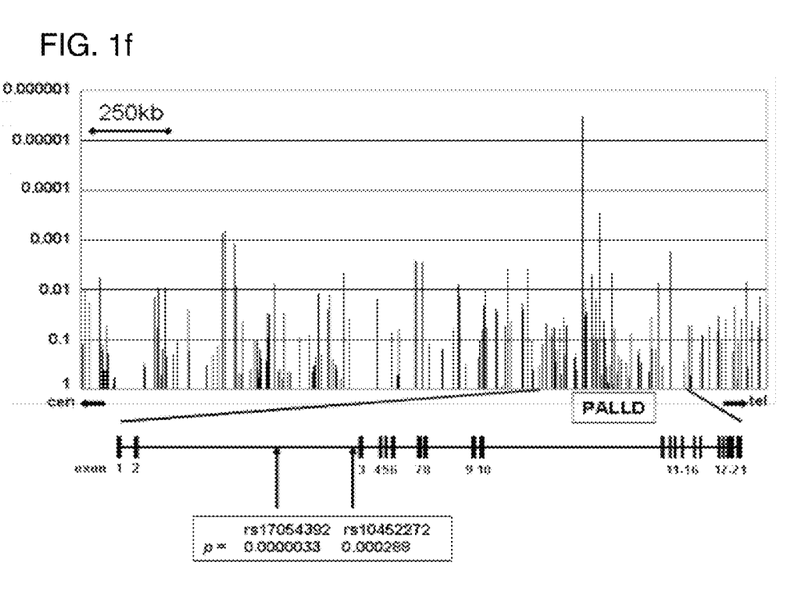

SNP rs17054392 is located within intron 2 of the paladin (PALLD) gene (FIG. 10, which codes for the cytoskeletal associated protein paladin, a component of actin-containing microfilaments that control cell shape, adhesion, and contraction. Patients who were heterozygous for rs17054392 had a mean QTcF change of −0.7 msec compared with 14.2 msec for patients with a different genotype (Table 1). Five other SNPs located in introns 2, 8, and 10 of PALLD also were significant at P<0.01. Previously, another polymorphism within intron 10 (rs12510359, not tested in our WGAS) had been associated with risk of myocardial infarction (FIG. 1d). The paladin protein is thought to play a critical role in cytoskeletal remodeling and to be able to respond to signals induced by vascular injury and signals that induce smooth muscle cell hypertrophy. The results described here suggest that PALLD may also affect myocardial repolarization.

Previous genetic research of QT prolongation has focused mainly on ion channel genes, but new genome-wide approaches provide the opportunity to identify genetic variants in unsuspected genes. Recently, a polymorphism that modulates cardiac repolarization was identified in a regulator of neuronal nitric oxide synthase. This WGAS of drug-induced QT prolongation, has identified several genetic polymorphisms associated with prolongation of the QT interval in patients with schizophrenia treated with iloperidone. These polymorphisms point to genes with a known or suspected myocardial role but not previously associated with cardiac repolarization or ventricular tachycardia. These results suggest the possible interplay of genes involved in the ceramide pathway (CERKL), prostaglandin transport (SLCO3A1), cardiac structure and function (BRUNOL4), cardiac development (NRG3), and myocardial infarction (PALLD) and of other genes such as NUBPL.

Patients 18 to 65 years of age with diagnoses of schizophrenia according to the *Diagnostic and Statistical Manual of Mental Disorders,* 4th Edition (disorganized [295.10], paranoid [295.30], or undifferentiated [295.90]) were eligible to participate in the trial. Patients were randomly assigned to iloperidone 12 mg twice a day (bid), ziprasidone 80 mg bid (active control), or placebo. Doses were titrated to their respective target doses from Days 1 to 7 and were maintained until Day 28. Participation in the pharmacogenomic analysis was optional. Blood samples were collected, and DNA was extracted (Quest Diagnostics Laboratories, Van Nuys, Calif.) from 432 of 457 patients who consented to the optional WGAS, including 218 patients administered iloperidone. Of these iloperidone-treated patients, 183 (152 men and 31 women) with QT data at Day 14 were part of the WGAS reported here. They included 16 Asian, 69 white, and 91 black or African American patients and 7 patients of other ethnic origins.

QT Interval

Twelve-lead ECG was performed at baseline and on Days 7, 14, 21, and 28. Except at baseline, ECG was performed 2 hours after patients had received the morning dose of study drug. ECG was performed 3 times at baseline and on Day 14, with single measurements obtained for other visits. QTc interval was calculated based on QTcF. The effect of iloperidone on QTc interval was measured by the mean change from baseline in Qtc.

Genotyping

DNA samples were genotyped for more than 500,000 SNPs with the use of an array set according to the manufacturer's instructions (GeneChip® Human Mapping 500K Array Set; Affymetrix, Santa Clara, Calif.). The set was composed of 2 arrays, each capable of genotyping on average 250,000 SNPs (approximately 262,000 for Nsp arrays and 238,000 for Sty arrays). To ensure the integrity of the data collected from DNA arrays, the following quality control steps were taken:

Algorithms

Each microarray (GeneChip® Human 500K Array Set; Affymetrix) was analyzed with the dynamic model-based genotyping algorithm and with the latest Bayesian robust linear model with Mahalanobis distance classifier (BRLMM); the confidence threshold was 0.5. Under these conditions, missing genotypes were assumed missing at random, and no imputation was made for any genetic data. The BRLMM Analysis Tool 2.0 and the SNP Signal Tool 1.0.0.12. (Affymetrix) were used to analyze and visualize the distribution and separation of genotype calls of individual SNPs.

Call Rate

Call rate was defined for a single array as the percentage of SNPs that were called AA, AB, or BB by the BRLMM algorithm. Only arrays with ≥93% call rate were retained for further analysis.

Concordance Between Arrays

Of the more than 500,000 SNPs genotyped, 50 were common to both the Sty and the Nsp arrays. Only arrays with greater than 90% concordance for these SNPs were used in further analysis.

Uniqueness of Samples

The approximately 250,000 SNP data obtained per sample on each array (Sty or Nsp) were compared with the genotypes of all other samples to identify potential duplicate samples. If more than 90% of the genotypes were identical between 2 arrays, DNA was retested to confirm genotypes and, if necessary, to eliminate duplicate samples.

Lack of DNA Contamination

Lack of DNA contamination of a sample by another sample was assessed for each array by determining the overall percentage of SNPs with heterozygote calls, as calculated by the dynamic model algorithm. Genotype calls from arrays with <30% heterozygote calls were considered to have come from a pure DNA sample. Only arrays with <30% heterozygote calls were used for further analysis.

Sex Determination

For each DNA sample, sex was blindly determined by the BRLMM algorithm based on the percentage of heterozygosity of the SNPs on the X chromosome. The result was compared with others for the expected sex. In case of divergent data, a polymerase chain reaction (PCR)-based assay for the amelogenin gene (AMELX) was performed on the original sample and on a new DNA aliquot. A new genotyping experiment was performed with the Sty and Nsp arrays. Samples with incompatible results were excluded from the WGAS.

Allele Frequency

This project focused on the most common polymorphisms by selection of SNPs that had a minor allele frequency of 10% or greater.

SNP Selection

A reference DNA (Human Genomic DNA 103 control; Affymetrix) with available genotypes for SNPs on the array set (GeneChip® Human 500K Array Set; Affymetrix) was systematically tested in parallel with the patients' samples. Eight DNA 103 replicates for both the Sty and the Nsp arrays were obtained and analyzed. Individual SNP assays were considered accurate when the genotype calls were identical across the 8 replicates and the reference provided by Affymetrix. Only SNPs with 100% concordance for DNA 103 were retained for the WGAS. Five SNPs that cross-hybridized with the Y chromosome and all SNPs on the X chromosome were not used. Total number of SNPs analyzed in this WGAS was 334,563.

DNA Sequencing

For each SNP of interest, a minimum of 15 DNA samples, including at least 5 samples for each homozygote and heterozygote genotype, were sequenced. The following primers were used for standard PCR amplification before sequencing:

5'-GGC CTT GAA AGT CTT GGA GC-3' (forward) and

5'-TGG AGG AGT GAG GAG ACC AG-3' (reverse) for rs4799915;

5'-CTT GAA ATA CAG TTG GCT TTG-3' (forward) and

5'-CAA GGT ACG ATA TGC ACA AAG-3' (reverse) for rs993648;

5'-GGG CTG ATT TAG AGG ATA TTG C-3' (forward) and

5'-TCC CAT CCT TGC TAT CTT AGT C-3' (reverse) for rs4933824;

5'-TGG AGA GGA GGA GAC CTA ATT G-3' (forward) and

5'-CCA AAC ACA TAT CCA ACC ATC-3' (reverse) for rs7142881;

5'-GCA CCC AGA GTT TCT TCC AG-3' (forward) and

5'-TTG GGC TGC CAA TTA TTC AC-3' (reverse) for rs17054392; and

5'-GTA GGA GGG AGG GCA AGA AC-3' (forward) and

5'-CAA TCC GGT GCC AGA GTC-3' (reverse) for rs3924426.

Sequencing was performed with a reagent kit (GeneAmp® PCR Reagent Kit with AmpliTaq DNA Polymerase; Applied Biosystems, Foster City, Calif.) according to the manufacturer's instructions for a 25-μL reaction. Nucleotide sequences were determined using an automated capillary DNA sequencer (Avant 3100; Applied Biosystems) and a cycle sequencing kit (BigDye® Terminator version 3.1 Cycle Sequencing Kit; Applied Biosystems) according to the manufacturer's instructions.

Genetic markers associated with prolongation of QTcF were identified through GLM analysis. The dependent variable was mean change from baseline to Day 14 because the effects on QT were greatest by Day 14, when iloperidone achieves steady state concentration. Baseline QTcF was used as a covariate, and genotype was used as the classifiable variable. The GLM used type 3 sums of squares, with all pairwise differences produced among the least squares means. Because 3 genetic models (AA vs non-AA; AB vs non-AB; BB vs non-BB) were tested for each of the 334,563 SNPs, a total of 1,003,689 tests were performed. The Benjamini and Hochberg (BH) procedure was used to control for the expected proportion of FDR. FDR corrections were obtained from PROC MULTTEST (SAS Institute, Cary, N.C.), which produces BH adjustments to original analytical P values. Significance thresholds of 0.1 and 0.25 have been used in the analysis of quantitative traits in case of large multiplicity problems. More recently, Benjamini and Yekutieli recommended not going higher than 0.2. Given that this study involved the performance of more than one million tests, the BH-adjusted threshold was set at P<0.2. For each SNP identified as a candidate biomarker of iloperidone-induced QT prolongation, post hoc analyses were conducted to investigate the effects of sex and race. No such effects were found.

The results of the WGAS offer the possibility of not only predicting the prolongation of an individual's QT interval in response to treatment with an antipsychotic or other compound capable of prolonging the QT interval, but of making such treatment more effective. For example, an individual predicted to exhibit above-average prolongation of the QT interval, based on the individual's genotype at one or more SNP locus described above, may be administered a lower dosage (e.g., between about 2 mg/day and about 24 mg/day, between about 5 mg/day and about 20 mg/day, or between about 10 mg/day and about 15 mg/day) than would otherwise be administered, thereby minimizing the possibility of any adverse side effects of such treatment. Similarly, an individual predicted to exhibit below-average prolongation of the QT interval may be administered a higher dosage (e.g., between about 24 mg/day and about 50 mg/day, between about 30 mg/day and about 50 mg/day, or between about 40 mg/day and about 50 mg/day) or may be treated with another compound not known to prolong the QT interval. If a patient's genotype at one or more SNP locus described above suggests that the patient is at risk for prolongation of the QT interval, the patient's treatment may include monitoring of the QT interval.

Alternatively, the dosage may be based on a patient's genotype at a particular SNP locus. For example, in one embodiment, the invention provides a method of treating a patient for one or more symptoms of a psychotic disorder, schizophrenia, or bipolar disorder, the method comprising: determining the patient's genotype in both copies of one single nucleotide polymorphism (SNP) locus selected from a group consisting of: rs993648, rs3924426, rs4799915, rs4933824, rs714881, and rs17054392; and in the case that the patient has a genotype that is associated with increased QT prolongation at the chosen SNP locus, administering to the patient an effective amount of an atypical antipsychotic based on the patient's rs993648, rs3924426, rs4799915, rs4933824, rs714881, or rs17054392 genotype.

An individual's genotype at one or more of the SNP loci described above may be determined by any number of methods. For example, the genotype(s) may be determined by analyzing the DNA sequence directly, as described above. Alternatively, the genotype(s) may be determined by analyzing an RNA transcript (e.g., mRNA) or a gene expression product (e.g., a protein), as will be recognized by one skilled in the art. Genotyping is preferably performed ex vivo.

An additional aspect of the invention is a kit for determining treatment strategy for a patient with a psychotic disorder or bipolar disorder. Such kit is useful, e.g., in predicting prolongation of the QT interval in response to treatment with, for example, an atypical antipsychotic, such as iloperidone, and, on the basis of such prognosis, treating the patient with a lower or higher dose of the atypical antipsychotic, treating the patient with an atypical antipsychotic in combination with other therapies, e.g., a typical antipsychotic, monitoring the patient's QT interval, or choosing a different treatment altogether.

A kit of the invention is a combination of physical elements, e.g., probes, including without limitation specific primers, labeled nucleic acid probes, antibodies, protein-capture agent(s), reagent(s), instruction sheet(s) and other elements useful to practice the invention, in particular, to identify the alleles present in the genetic loci described herein.

A kit of the invention may include at least one reagent specific for detecting a patient's genotype at least one of the relevant genetic loci, as described elsewhere herein. Detection can be direct, e.g., by directly sequencing the relevant portion of a person's chromosomal DNA, or indirect, e.g., by sequencing messenger RNA transcripts or by sequencing gene expression products, i.e., polypeptides. Thus, the reagent may be, e.g., a polynucleotide, or an array of polynucleotides, or an antibody or a panel of antibodies.

The kit may also comprise one or more gene specific genotyping primer composition. The primer composition can comprise at least one gene specific genotyping polynucleotide. The composition can comprise two or more sets of allele specific primer pairs. The two allele specific genotyping oligonucleotides may be packaged in separate containers. In some embodiments, degenerate primer sets are provided for amplification.

In another embodiment, the kit may optionally include instructions for isoelectric focusing methods for detecting and distinguishing gene expression products.

Antibody based kits can comprise, e.g., an antibody that is specific for the gene expression product of a given allele and that is bound to a solid support; and a second antibody that binds the gene expression product and that is conjugated to a detectable group.

The kit may also comprise reagents such as buffering agents, hybridization buffers, and protein or nucleic acid stabilizing agents, e.g., polysaccharides and the like. If carrying out the assay requires amplification of DNA or RNA, such as by PCR, then the kit may also comprise a polymerase or a reaction buffer. The kit may be packaged in any suitable manner, typically with all elements in a single container along with a sheet of printed instructions for carrying out the test or for interpreting results.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

TABLE 1

SNPs Significantly Associated With Change in QT in the Iloperidone-Treated Patients

| SNP | Gene | Location | Position | Genotype$^a$ | N$^a$ | Mean$^a$ | SD$^a$ | P | BH-adjusted P |
|---|---|---|---|---|---|---|---|---|---|
| rs993648 | CERKL | 2q31.3 | 182281500 | TT | 44 | 18.72 | 13.27 | 0.00000283 | 0.16 |
|  |  |  |  | CT$^b$ | 80 | 4.50 | 14.92 |  |  |
|  |  |  |  | CC | 50 | 17.02 | 20.50 |  |  |
|  |  |  |  | Non-CT$^c$ | 94 | 17.81 | 17.42 |  |  |
| rs3924426 | SLCO3A1 | 15q26.1 | 90246877 | TT$^c$ | 135 | 14.99 | 17.02 | .00000216 | 0.16 |
|  |  |  |  | CT | 43 | 3.64 | 14.04 |  |  |
|  |  |  |  | CC | 5 | −7.00 | 15.19 |  |  |
|  |  |  |  | Non-TT$^b$ | 48 | 2.53 | 14.37 |  |  |
| rs4799915 | BRUNOL4 | 18q12.2 | 33182637 | TT | 54 | 15.81 | 17.00 | .00000354 | 0.17 |
|  |  |  |  | CT | 78 | 13.52 | 16.37 |  |  |
|  |  |  |  | CC$^b$ | 48 | 2.88 | 15.45 |  |  |
|  |  |  |  | Non-CC$^c$ | 132 | 14.46 | 16.60 |  |  |
| rs4933824 | NRG3 | 10q23.1 | 83809105 | GG$^c$ | 124 | 15.33 | 16.56 | .00000211 | 0.16 |
|  |  |  |  | GT | 47 | 4.62 | 16.71 |  |  |
|  |  |  |  | TT | 10 | 3.41 | 16.01 |  |  |
|  |  |  |  | Non-GG$^b$ | 57 | 4.41 | 16.45 |  |  |
| rs7142881 | NUBPL | 14q12 | 31163299 | GG$^b$ | 79 | 5.67 | 14.73 | .00000160 | 0.15 |
|  |  |  |  | AG | 71 | 16.35 | 17.44 |  |  |
|  |  |  |  | AA | 28 | 17.65 | 19.14 |  |  |
|  |  |  |  | Non-GG$^c$ | 99 | 16.71 | 17.85 |  |  |
| rs17054392 | PALLD | 4q32.3 | 169904988 | TT | 151 | 14.12 | 17.03 | .00000330 | 0.17 |
|  |  |  |  | CT$^b$ | 30 | −0.69 | 12.65 |  |  |
|  |  |  |  | CC | 2 | 17.33 | 18.38 |  |  |
|  |  |  |  | Non-CT$^c$ | 153 | 14.16 | 16.99 |  |  |

SNPs are identified by their unique dbSNP number (http://www.ncbi.nlm.nih.gov/projects/SNP/) and are listed in ascending order of dbSNP number.
The gene name corresponds to the NCBI official symbol of the gene where the SNP is located.
The location and position of each SNP in the genome are indicated by the cytogenetic location and the physical position, as listed in the NCBI Build 36.1, March 2006 (http://www.ncbi.nlm.nih.gov/entrez/query.fcgi?db=snp).
Raw P values are based on GLM analysis.
BH-adjusted P values are based on FDR correction.
$^a$Genotypes corresponding to the DNA + strand.
$^{b,c}$Genotype classes associated with the lowest and highest mean increased QT, respectively, used in the GLM analysis. Number of patients (N), mean change in QT in msec (mean), and standard deviation (SD) are shown for each genotype class.

What is claimed is:

1. A method of treating a human patient for one or more symptoms of a psychotic disorder, the method comprising:
determining, from a biological sample of the patient, the patient's genotype in both copies of the single nucleotide polymorphism (SNP) locus rs3924426; and
treating the patient based upon whether the patient's genotype at the rs3924426 SNP locus is associated with increased QT prolongation, wherein treating includes:
in the case that the patient has a TT genotype at the rs3924426 SNP locus, administering to the patient an effective amount of iloperidone or a pharmaceutically-acceptable salt thereof, the effective amount being less than would be administered to a patient who does not have a TT genotype at the rs3924426 SNP locus; or
in the case that the patient does not have a TT genotype at the rs3924426 SNP locus, administering to the patient an increased amount of iloperidone, the increased amount being more than would be administered to a patient who has a TT genotype at the rs3924426 SNP locus.

2. The method of claim 1, wherein the effective amount is between about 2 mg/day and about 24 mg/day.

3. The method of claim 2, wherein the effective amount is between about 5 mg/day and about 20 mg/day.

4. The method of claim 3, wherein the effective amount is between about 10 mg/day and about 15 mg/day.

5. The method of claim 1, wherein the increased amount is between about 24 mg/day and about 50 mg/day.

6. The method of claim 5, wherein the increased amount is between about 30 mg/day and about 50 mg/day.

7. The method of claim 6, wherein the increased amount is between about 40 mg/day and about 50 mg/day.

8. The method of claim 1, wherein treating the patient includes monitoring the patient for QT prolongation.

* * * * *

UNITED STATES PATENT AND TRADEMARK OFFICE
CERTIFICATE OF CORRECTION

PATENT NO. : 8,652,776 B2  
APPLICATION NO. : 12/675607  
DATED : February 18, 2014  
INVENTOR(S) : Christian Lavedan et al.

Page 1 of 1

It is certified that error appears in the above-identified patent and that said Letters Patent is hereby corrected as shown below:

In the Specification

Column 1, line 14

Delete: "Seq_Ms"  
Insert: -- Seq_IDs --

Column 7, line 5

Delete: "FIG. 10"  
Insert: -- FIG. 1C --

Signed and Sealed this  
Third Day of June, 2014

Michelle K. Lee  
*Deputy Director of the United States Patent and Trademark Office*

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: primer sequence

<400> SEQUENCE: 1
ggccttgaaa gtcttggagc                                                      20

<210> SEQ ID NO 2
<211> LENGTH: 20
<212> TYPE: DNA
<213> ORGANISM: Artificial Sequence
<220> FEATURE:
<223> OTHER INFORMATION: primer sequence

<400> SEQUENCE: 2
tggaggagtg aggagaccag                                                      20

<210> SEQ ID NO 3
<211> LENGTH: 21
<212> TYPE: DNA
<213> ORGANISM: Artificial Sequence
<220> FEATURE:
<223> OTHER INFORMATION: primer sequence

<400> SEQUENCE: 3
cttgaaatac agttggcttt g                                                    21

<210> SEQ ID NO 4
<211> LENGTH: 21
<212> TYPE: DNA
<213> ORGANISM: Artificial Sequence
<220> FEATURE:
<223> OTHER INFORMATION: primer sequence

<400> SEQUENCE: 4
caaggtacga tatgcacaaa g                                                    21

<210> SEQ ID NO 5
<211> LENGTH: 22
<212> TYPE: DNA
<213> ORGANISM: Artificial Sequence
<220> FEATURE:
<223> OTHER INFORMATION: primer sequence

<400> SEQUENCE: 5
gggctgattt agaggatatt gc                                                   22

<210> SEQ ID NO 6
<211> LENGTH: 22
<212> TYPE: DNA
<213> ORGANISM: Artificial Sequence
<220> FEATURE:
<223> OTHER INFORMATION: primer sequence

<400> SEQUENCE: 6
tcccatcctt gctatcttag tc                                                   22

<210> SEQ ID NO 7
<211> LENGTH: 22
<212> TYPE: DNA
```

-continued

```
<213> ORGANISM: Artificial Sequence
<220> FEATURE:
<223> OTHER INFORMATION: primer sequence

<400> SEQUENCE: 7
tggagaggag gagacctaat tg                                                22

<210> SEQ ID NO 8
<211> LENGTH: 21
<212> TYPE: DNA
<213> ORGANISM: Artificial Sequence
<220> FEATURE:
<223> OTHER INFORMATION: primer sequence

<400> SEQUENCE: 8
ccaaacacat atccaaccat c                                                 21

<210> SEQ ID NO 9
<211> LENGTH: 20
<212> TYPE: DNA
<213> ORGANISM: Artificial Sequence
<220> FEATURE:
<223> OTHER INFORMATION: primer sequence

<400> SEQUENCE: 9
gcacccagag tttcttccag                                                   20

<210> SEQ ID NO 10
<211> LENGTH: 20
<212> TYPE: DNA
<213> ORGANISM: Artificial Sequence
<220> FEATURE:
<223> OTHER INFORMATION: primer sequence

<400> SEQUENCE: 10
ttgggctgcc aattattcac                                                   20

<210> SEQ ID NO 11
<211> LENGTH: 20
<212> TYPE: DNA
<213> ORGANISM: Artificial Sequence
<220> FEATURE:
<223> OTHER INFORMATION: primer sequence

<400> SEQUENCE: 11
gtaggaggga gggcaagaac                                                   20

<210> SEQ ID NO 12
<211> LENGTH: 18
<212> TYPE: DNA
<213> ORGANISM: Artificial Sequence
<220> FEATURE:
<223> OTHER INFORMATION: primer sequence

<400> SEQUENCE: 12
caatccggtg ccagagtc                                                     18
```